(12) United States Patent
Ma et al.

(10) Patent No.: US 10,780,057 B2
(45) Date of Patent: Sep. 22, 2020

(54) CASEIN-BASED SILICA DUAL DRUG-LOADING COMPOSITE MICROCAPSULE AND PREPARATION METHOD THEREFOR

(71) Applicants: SHAANXI UNIVERSITY OF SCIENCE & TECHNOLOGY, Xi'an (CN); Jianzhong Ma, Xi'an (CN); Qianqian Fan, Xi'an (CN); Qunna Xu, Xi'an (CN)

(72) Inventors: Jianzhong Ma, Xi'an (CN); Qianqian Fan, Xi'an (CN); Qunna Xu, Xi'an (CN)

(73) Assignee: SHAANXI UNIVERSITY OF SCIENCE & TECHNOLOGY, Xi'an (CN)

( * ) Notice: Subject to any disclaimer, the term of this patent is extended or adjusted under 35 U.S.C. 154(b) by 13 days.

(21) Appl. No.: 16/348,873

(22) PCT Filed: Jan. 13, 2017

(86) PCT No.: PCT/CN2017/071043
§ 371 (c)(1),
(2) Date: May 10, 2019

(87) PCT Pub. No.: WO2018/086248
PCT Pub. Date: May 17, 2018

(65) Prior Publication Data
US 2019/0274966 A1    Sep. 12, 2019

(30) Foreign Application Priority Data
Nov. 11, 2016  (CN) .......................... 2016 1 0992992

(51) Int. Cl.
*A61K 9/50*   (2006.01)
*A61K 47/02*  (2006.01)
*A61K 47/24*  (2006.01)

(52) U.S. Cl.
CPC .......... *A61K 9/5052* (2013.01); *A61K 9/5084* (2013.01); *A61K 9/5089* (2013.01); *A61K 47/02* (2013.01); *A61K 47/24* (2013.01)

(58) Field of Classification Search
CPC ........................... A61K 9/5052; A61K 9/5089
See application file for complete search history.

(56) References Cited

FOREIGN PATENT DOCUMENTS

CN          104825421 A    *   8/2015

OTHER PUBLICATIONS

Machine translation of CN-104825421-A, pp. 1-6, 2015 (Year: 2015).*

* cited by examiner

*Primary Examiner* — Andrew S Rosenthal
(74) *Attorney, Agent, or Firm* — CBM Patent Consulting, LLC

(57) ABSTRACT

This invention presents a method for preparing casein-based silica dual drug-loaded composite microcapsule. Recently, casein has shown good application prospects in the field of medicine due to its good biocompatibility and unique cavity structure. However, research on preparation of casein-based dual drug-loaded microcapsules is still rarely reported. In this invention, dual drug-loaded casein microcapsules is obtained via interfacial polymerization method, where drug-loaded casein can be used as outer shell material in capsule, and silica is served as inner shell in the capsule. In the obtained microcapsule, drugs can not only be loaded in the inner cavity, but also in casein shell. Application of the dual drug-loaded microcapsules in the treatment of diseases is expected to reduce the number of dose to a certain extent and improve the therapeutic effect.

6 Claims, 1 Drawing Sheet

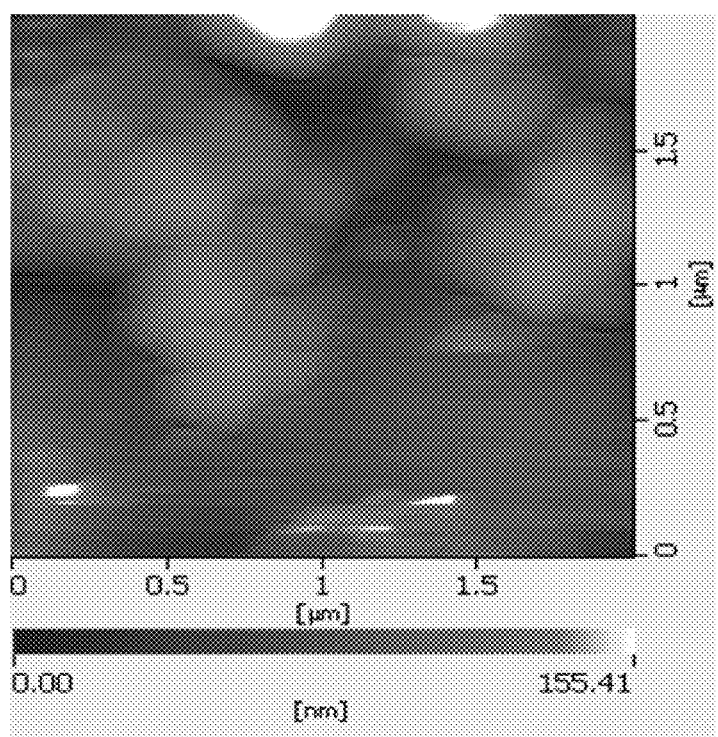

CASEIN-BASED SILICA DUAL DRUG-LOADING COMPOSITE MICROCAPSULE AND PREPARATION METHOD THEREFOR

TECHNICAL FIELD

The present intention involves a dual drug-loaded microcapsule, in particular involves casein-based silica dual drug-loaded composite microcapsule and its preparation method.

BACKGROUND

Microcapsule is a micro-container with polymer or composite material as shells, which can be used for drug encapsulation, thereby slowing down or controlling release rate of drugs in vivo, thus improving the therapeutic effect. It has been widely used in the development of pharmaceutical products. However, the traditional microcapsules can only load a single drug, which limits the scope of application and therapeutic effect. Therefore, it is urgent to develop dual drug-loaded microcapsules.

Casein is a natural protein extracted from milk. It possesses good biocompatibility and good biodegradability, and these special properties make it popular in the development of pharmaceutical microcapsules. At the same time, the cavity structure of casein itself can also render it a certain loading function, which is beneficial to its application in the field of medicine.

In recent years, drug carriers with dual drug-loading functions have been gradually proposed. The novel carrier can simultaneously achieve loading and controlled release of two drugs, reduce the number of dose, and enhance the dosing efficiency effectively, thereby greatly improving the therapeutic effect. (Xiaodan Wang, et al. A versatile platform of magnetic microspheres loaded with dual-anticancer drugs for drug release, Materials Chemistry and Physics, 2016, 177: 213-219). However, there are few studies about the dual drug-loaded microcapsule that combined casein shell and the inner cavity of capsule.

Recently, novel microcapsules composed of organic/inorganic composite shell have been developed successfully. Those novel microcapsules combine the advantages of organic microcapsules and inorganic microcapsules, holding much promise in pharmaceuticals, food, textile, and so on. (Jiafu Shi, et al. Design and synthesis of organic-inorganic hybrid capsules for biotechnological applications, Chem. Soc. Rev., 2014, 43(15): 5192-5210). However, casein-based silica dual drug-loaded composite microcapsule using casein and silica as shells has been rarely reported.

Technical Problem

This intention aims at providing a method for preparing casein-based silica dual drug-loaded composite microcapsule, the obtained microcapsules show good stability, and can load dual drugs simultaneously, thus achieving the controlled release of drugs.

Solution for the Problem

A method for preparing a casein-based silica dual drug-loaded composite microcapsule comprises:

step 1: adding casein into 2-4 wt % of acid solution, the mass ratio of casein to acid solution is 1:100-1000, stirring the solution for 3 to 6 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is (1-12 mg):(20-100 μL), ultrasonically treating the drug-casein mixture for 5-20 min after stirring, and obtaining a drug-loaded casein solution; wherein the mass ratio of casein to hydrophobic drug A is 1-10:1;

step 2: adding the amphiphilic block copolymer and hydrophobic drug B simultaneously to 400-600 μL of an organic solvent, and stirring at room temperature for 10-15 hours to obtain a mixed solution A, the mass-mass-volume ratio of amphiphilic block copolymer, hydrophobic drug B to organic solvent is 4-10 mg: 1-8 mg: 40-60 μL;

step 3: adding $SiO_2$ precursor and silane coupling agent to the mixed solution A, and stirring at room temperature for 15-40 min to obtain a mixed solution B; the volume ratio of $SiO_2$ precursor, silane coupling agent to the mixed solution A is 5-8:2-5:50-70 μL;

step 4: then, adding 20-100 μL of the mixed solution B to 40-70 mL of the drug-loaded casein solution in a stirred state by a pipette at each interval of 5-10 min, the stirring speed is 300-1000 r/min; then, stirring above mixture continuously at room temperature for 5 to 7 days to obtain the casein-based $SiO_2$ dual drug-loaded composite microcapsule.

In step 1, casein is food grade or biological grade; the acid used is hydrochloric acid, formic acid, acetic acid, citric acid or boric acid; hydrophobic drug A is vitamin A, ibuprofen, aspirin, curcumin, doxorubicin, ginsenoside, salicylic acid or aclarithromycin; organic solvent is ethanol, diethyl ether, tetrahydrofuran, dichloroethane or n-hexane;

In step 2, amphiphilic block copolymer is selected from the group consisting of A-B-A and A-B-C triblock copolymers, wherein A and C are hydrophilic segments and B is hydrophobic segments; hydrophobic drug B is curcumin, doxorubicin, ginsenoside, vitamin A, ibuprofen, aspirin, salicylic acid or aclaramicin; organic solvent used in step 2 is tetrahydrofuran, dichloroethane, diethyl ether or n-hexane.

In step 3, a precursor of $SiO_2$ is methyl orthosilicate or ethyl orthosilicate; the silane coupling agent is vinyl triethoxysilane, γ-aminopropyltrimethoxysilane, γ-methacryloxypropyltrimethoxysilane, 3-aminopropyltriethoxysilane or vinyl trimethoxysilane.

Microcapsules which are prepared by the method have an outer shell and an inner cavity that helps load and releases drugs.

Advantageous Effects of the Invention

In this invention, natural product, casein, has been utilized to load hydrophobic drugs, and the drug-loaded casein is used as capsule shell, then $SiO_2$ precursor and the other hydrophobic drug are introduced to obtain dual drug-loaded casein-based $SiO_2$ microcapsules by interfacial polymerization method. Drugs can not only be loaded in the inner cavity of the microcapsule, but also in the outer shell of casein, thus realizing the loading and sustained release of two drugs at the same time.

DESCRIPTION OF FIGURE

FIG. 1. Atomic force microscope images of as-prepared dual drug-loaded casein-based $SiO_2$ microcapsules

EXAMPLES OF THE INTENTION

Detailed description of the invention is given below with reference to the specific embodiments.

At present, there are no reports on the preparation of casein-based SiO$_2$ dual drug-loaded microcapsules by interfacial polymerization, where casein is used as a drug carrier and capsule shell material simultaneously. Application of such dual drug-loaded microcapsules is expected to improve the therapeutic effect and reduce the number of doses to the patient.

A method for preparing a casein-based silica dual drug-loaded composite microcapsule comprises:

step 1: adding casein into 2-4 wt % of acid solution, the mass ratio of casein to acid solution is 1:100-1000, stirring the solution for 3 to 6 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is (1-12 mg):(20-100 μL), ultrasonically treating the drug-casein mixture for 5-20 min after stirring, and obtaining a drug-loaded casein solution; wherein the mass ratio of casein to hydrophobic drug A is 1-10:1;

step 2: adding the amphiphilic block copolymer and hydrophobic drug B simultaneously to 400-600 μL of an organic solvent, and stirring at room temperature for 10-15 hours to obtain a mixed solution A, the mass-mass-volume ratio of amphiphilic block copolymer, hydrophobic drug B to organic solvent is 4-10 mg: 1-8 mg: 40-60 μL;

step 3: adding SiO$_2$ precursor and silane coupling agent to the mixed solution A, and stirring at room temperature for 15-40 min to obtain a mixed solution B; the volume ratio of SiO$_2$ precursor, silane coupling agent to the mixed solution A is 5-8:2-5:50-70 μL;

step 4: then, adding 20-100 μL of the mixed solution B to 40-70 mL of the drug-loaded casein solution in a stirred state by a pipette at each interval of 5-10 min, the stirring speed is 300-1000 r/min; then, stirring above mixture continuously at room temperature for 5 to 7 days to obtain the casein-based SiO$_2$ dual drug-loaded composite microcapsule.

In step 1, casein is food grade or biological grade; the acid used is hydrochloric acid, formic acid, acetic acid, citric acid or boric acid; hydrophobic drug A is vitamin A, ibuprofen, aspirin, curcumin, doxorubicin, ginsenoside, salicylic acid or aclarithromycin; organic solvent is ethanol, diethyl ether, tetrahydrofuran, dichloroethane or n-hexane;

In step 2, amphiphilic block copolymer is selected from the group consisting of A-B-A and A-B-C triblock copolymers, wherein A and C are hydrophilic segments and B is hydrophobic segments; hydrophobic drug B is curcumin, doxorubicin, ginsenoside, vitamin A, ibuprofen, aspirin, salicylic acid or aclaramicin; organic solvent used in step 2 is tetrahydrofuran, dichloroethane, diethyl ether or n-hexane.

In step 3, a precursor of SiO$_2$ is methyl orthosilicate or ethyl orthosilicate; the silane coupling agent is vinyl triethoxysilane, γ-aminopropyltrimethoxysilane, γ-methacryloxypropyltrimethoxysilane, 3-aminopropyltriethoxysilane or vinyl trimethoxysilane.

Microcapsules which are prepared by the method have an outer shell and an inner cavity that helps load and releases drugs.

Example 1

A method for preparing a casein-based silica dual drug-loaded composite microcapsule comprises:

step 1: adding casein into 2 wt % of acid solution, the mass ratio of casein to acid solution is 1:1000, stirring the solution for 3 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is 12 mg: 20 μL), ultrasonically treating the drug-casein mixture for 20 min after stirring, and obtaining a drug-loaded casein solution; wherein the mass ratio of casein to hydrophobic drug A is 1:1;

step 2: adding the amphiphilic block copolymer and hydrophobic drug B simultaneously to 600 μL of an organic solvent, and stirring at room temperature for 10 hours to obtain a mixed solution A, the mass-mass-volume ratio of amphiphilic block copolymer, hydrophobic drug B to organic solvent is 10 mg:1 mg:60 μL;

step 3: adding SiO$_2$ precursor and silane coupling agent to the mixed solution A, and stirring at room temperature for 15 min to obtain a mixed solution B; the volume ratio of SiO$_2$ precursor, silane coupling agent to the mixed solution A is 8:2:70 μL;

step 4: then, adding 100 μL of the mixed solution B to 40 mL of the drug-loaded casein solution in a stirred state by a pipette at each interval of 5 min, the stirring speed is 1000 r/min; then, stirring above mixture continuously at room temperature for 5 days to obtain the casein-based SiO$_2$ dual drug-loaded composite microcapsule.

In step 1, casein is food grade; the acid used is hydrochloric acid, or formic acid; hydrophobic drug A is vitamin A, ibuprofen, or aspirin; organic solvent is ethanol, or diethyl ether;

In step 2, amphiphilic block copolymer is selected from the group consisting of A-B-A, wherein A is hydrophilic segment and B is hydrophobic segment; hydrophobic drug B is curcumin, doxorubicin, or ginsenoside; organic solvent used in step 2 is tetrahydrofuran, or dichloroethane.

In step 3, a precursor of SiO$_2$ is methyl orthosilicate; the silane coupling agent is vinyl triethoxysilane, or γ-aminopropyltrimethoxysilane.

Microcapsules which are prepared by the method have an outer shell and an inner cavity that helps load and releases drugs.

Example 2

A method for preparing a casein-based silica dual drug-loaded composite microcapsule comprises:

step 1: adding casein into 3 wt % of acid solution, the mass ratio of casein to acid solution is 1:500, stirring the solution for 4.5 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is 6 mg: 60 μL, ultrasonically treating the drug-casein mixture for 10 min after stirring, and obtaining a drug-loaded casein solution; wherein the mass ratio of casein to hydrophobic drug A is 5:1;

step 2: adding the amphiphilic block copolymer and hydrophobic drug B simultaneously to 500 μL of an organic solvent, and stirring at room temperature for 12 hours to obtain a mixed solution A, the mass-mass-volume ratio of amphiphilic block copolymer, hydrophobic drug B to organic solvent is 7 mg:4 mg:50 μL;

step 3: adding SiO$_2$ precursor and silane coupling agent to the mixed solution A, and stirring at room temperature for 25 min to obtain a mixed solution B; the volume ratio of SiO$_2$ precursor, silane coupling agent to the mixed solution A is 6:3:60 μL;

step 4: then, adding 60 μL of the mixed solution B to 55 mL of the drug-loaded casein solution in a stirred state by a pipette at each interval of 7 min, the stirring speed is 600 r/min; then, stirring above mixture continuously at room temperature for 6 days to obtain the casein-based $SiO_2$ dual drug-loaded composite microcapsule.

In step 1, casein is biological grade; the acid used is acetic acid, or citric acid; hydrophobic drug A is curcumin, doxorubicin, or ginsenoside; organic solvent is tetrahydrofuran, or dichloroethane;

In step 2, amphiphilic block copolymer is selected from the group consisting of A-B-C triblock copolymers, wherein A and C are hydrophilic segments and B is hydrophobic segment; hydrophobic drug B is vitamin A, ibuprofen, or aspirin; organic solvent used in step 2 is diethyl ether.

In step 3, a precursor of $SiO_2$ is ethyl orthosilicate; the silane coupling agent is γ-methacryloxypropyltrimethoxysilane, or 3-aminopropyl-triethoxysilane or vinyl trimethoxysilane.

Microcapsules which are prepared by the method have an outer shell and an inner cavity that helps load and releases drugs.

Example 3

A method for preparing a casein-based silica dual drug-loaded composite microcapsule comprises:

step 1: adding casein into 4 wt % of acid solution, the mass ratio of casein to acid solution is 1:100, stirring the solution for 6 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is 1 mg:100 μL, ultrasonically treating the drug-casein mixture for 5 min after stirring, and obtaining a drug-loaded casein solution; wherein the mass ratio of casein to hydrophobic drug A is 10:1;

step 2: adding the amphiphilic block copolymer and hydrophobic drug B simultaneously to 400 μL of an organic solvent, and stirring at room temperature for 15 hours to obtain a mixed solution A, the mass-mass-volume ratio of amphiphilic block copolymer, hydrophobic drug B to organic solvent is 4 mg:8 mg:40 μL;

step 3: adding $SiO_2$ precursor and silane coupling agent to the mixed solution A, and stirring at room temperature for 40 min to obtain a mixed solution B; the volume ratio of $SiO_2$ precursor, silane coupling agent to the mixed solution A is 5:5:50 μL;

step 4: then, adding 20 μL of the mixed solution B to 70 mL of the drug-loaded casein solution in a stirred state by a pipette at each interval of 10 min, the stirring speed is 300 r/min; then, stirring above mixture continuously at room temperature for 7 days to obtain the casein-based $SiO_2$ dual drug-loaded composite microcapsule.

In step 1, casein is biological grade; the acid used is boric acid; hydrophobic drug A is salicylic acid, or aclarithromycin; organic solvent is n-hexane;

In step 2, amphiphilic block copolymer is selected from the group consisting of A-B-C triblock copolymers, wherein A and C are hydrophilic segments and B is hydrophobic segment; hydrophobic drug B is salicylic acid, or aclaramicin; organic solvent used in step 2 is n-hexane;

In step 3, a precursor of $SiO_2$ is ethyl orthosilicate; the silane coupling agent is vinyl trimethoxysilane.

Microcapsules which are prepared by the method have an outer shell and an inner cavity that helps load and releases drugs.

TABLE 1

Loading efficiency and cumulative release rate (after 40 h) of drugs in casein-based silica dual drug-loaded composite microcapsule

| Drug | Drug loading efficiency (%) | 40 h cumulative release rate (%) |
|---|---|---|
| Drug A: ibuprofen | 69 | 88 |
| Drug B: aspirin | 86 | 60 |

The samples used in Table 1 were the casein-based $SiO_2$ dual-loaded microcapsules obtained by loading the drug A-buprofen on the outer wall of the capsule and the drug B aspirin in the core of the capsule. It can be seen from Table 1 that the obtained microcapsules can simultaneously load ibuprofen and aspirin, and comparing the loading and sustained release effects of the two drugs, it can be found that the loading efficiency of drug B aspirin is higher and the release rate in the capsule core is slow, 40 h cumulative release rate is only 60%.

The content of the present invention is not limited to the embodiments, and any equivalent changes to the technical solutions of the present invention will be covered by the claims of the present invention.

What is claimed is:

1. A method for preparing a casein-based silica dual drug-loaded composite microcapsule comprises:
   step 1: adding casein into 2-4 wt % of acid solution, the mass ratio of casein to acid solution is 1:100-1000, stirring the solution for 3 to 6 hours at room temperature to obtain a casein solution; dissolving hydrophobic drug A in organic solvent as a drug solution, adding the drug solution into the casein solution as a drug-casein mixture, and the mass-to-volume ratio of the hydrophobic drug A to organic solvent is (1-12 mg):(20-100 μL), ultrasonically treating the drug-casein mixture for 5-20 min after stirring, and obtaining a drug-loaded casein solution; wherein the mass ratio of casein to hydrophobic drug A is 1-10:1;
   step 2: adding the amphiphilic block copolymer and hydrophobic drug B simultaneously to 400-600 μL of an organic solvent, and stirring at room temperature for 10-15 hours to obtain a mixed solution A, the mass-mass-volume ratio of amphiphilic block copolymer, hydrophobic drug B to organic solvent is 4-10 mg:1-8 mg:40-60 μL;
   step 3: adding $SiO_2$ precursor and silane coupling agent to the mixed solution A, and stirring at room temperature for 15-40 min to obtain a mixed solution B; the volume ratio of $SiO_2$ precursor, silane coupling agent to the mixed solution A is 5-8:2-5:50-70 μL;
   step 4: then, adding 20-100 μL of the mixed solution B to 40-70 mL of the drug-loaded casein solution in a stirred state by a pipette at each interval of 5-10 min, the stirring speed is 300-1000 r/min; then, stirring above mixture continuously at room temperature for 5 to 7 days to obtain the casein-based $SiO_2$ dual drug-loaded composite microcapsule.

2. The method according to claim 1, wherein in step 1, casein is food grade or biological grade; the acid used is hydrochloric acid, formic acid, acetic acid, citric acid or boric acid; hydrophobic drug A is vitamin A, ibuprofen, aspirin, curcumin, doxorubicin, ginsenoside, salicylic acid or aclarithromycin; organic solvent is ethanol, diethyl ether, tetrahydrofuran, dichloroethane or n-hexane.

3. The method according to claim 1, wherein in step 2, amphiphilic block copolymer is selected from the group consisting of A-B-A and A-B-C triblock copolymers, wherein A and C are hydrophilic segments and B is hydrophobic segments; hydrophobic drug B is curcumin, doxorubicin, ginsenoside, vitamin A, ibuprofen, aspirin, salicylic acid or aclaramicin; organic solvent used in step 2 is tetrahydrofuran, dichloroethane, diethyl ether or n-hexane.

4. The method according to claim 1, wherein in step 3, a precursor of $SiO_2$ is methyl orthosilicate or ethyl orthosilicate; the silane coupling agent is vinyl triethoxysilane, γ-aminopropyltrimethoxysilane, γ-methacryloxypropyltrimethoxysilane, 3-aminopropyltriethoxysilane or vinyl trimethoxysilane.

5. Microcapsules which are prepared by the method of claim 1.

6. The microcapsules according to claim 5, wherein the microcapsules have an outer shell and an inner cavity that helps load and releases drugs.

* * * * *